United States Patent [19]

Ibrahim

[11] Patent Number: 5,098,911
[45] Date of Patent: Mar. 24, 1992

[54] HEMIHYDRATE OF 4-(5,6,7,8-TETRAHYDROIMIDAZO[1,5−A]-PYRIDIN-5-N) BENZONITRILE HYDROCHLORIDE

[75] Inventor: Jutta Ibrahim, Ramlinsburg, Switzerland

[73] Assignee: CIBA-GEIGY Corporation, Ardsley, N.Y.

[21] Appl. No.: 636,816

[22] Filed: Jan. 2, 1991

[30] Foreign Application Priority Data

Jan. 12, 1990 [CH] Switzerland ............................ 100/90

[51] Int. Cl.$^5$ ..................... A61K 31/435; C07D 47/04
[52] U.S. Cl. ..................................... 514/300; 546/121
[58] Field of Search ......................... 546/121; 514/300

[56] References Cited

U.S. PATENT DOCUMENTS 4,617,307 10/1991 Browne ................................ 546/121

FOREIGN PATENT DOCUMENTS 114573 8/1984 European Pat. Off. .
165904 12/1985 European Pat. Off. .

OTHER PUBLICATIONS

Lang et al., Cancer Res. 31, 220, Abs. 1305 (1990) Corresponding to Poster No. 1305.
Santen et al., J. Clin. Endocrin., and Metabolism 68, 99–106 (1989).
Dowsett, et al., J. Endocrinol. 119 (Supp) Abs. 123 (1988).
Santen, et al., Clin. Res. 37, 535A (1989).
Demers, et al., J. Clin Endocrinol. 70, 1162–1166 (1990).
Juniewicz, et al., Ann. NY Acad. Sci. 513, 337–339 (1987).
Schieweck, et al., Proc. Am. Assoc. Cancer Res. 30, 303 (1989).
Oral Presentation of Hanagan, 6 Oct. 1988 Pretoria, South Africa.
Lamberts, et al., Chem. Abs. 111, 187280s (1989).
Santen, et al., Abstract of Oral presentation at 70th Annual Meeting of the Endocrine Society.

*Primary Examiner*—Bernard Dentz
*Attorney, Agent, or Firm*—Irving M. Fishman; Karen G. Kaiser

[57] ABSTRACT

The invention relates to a novel crystalline form, containing water of crystallization, of 4-(5,6,7,8-tetrahydroimidazol[1,5- a]pyridin-5-yl)-benzonitrile hydrochloride of formula Ia (Ia)

and to a process for the preparation thereof. The novel crystalline form is distinguished by excellent storage stability.

6 Claims, No Drawings

HEMIHYDRATE OF 4-(5,6,7,8-TETRAHYDROIMIDAZO[1,5-A]PYRIDIN-5-YL)BENZONITRILE HYDROCHLORIDE

The invention relates to a novel crystalline form, containing water of crystallisation, of 4-(5,6,7,8-tetrahydroimidazo[1,5-a]pyridin-5-yl)-benzonitrile hydrochloride of formula Ia

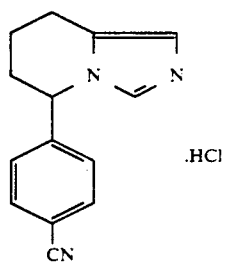

(Ia)

to process for the preparation thereof, to pharmaceutical preparations containing that crystalline form, and to the use thereof for the therapeutic treatment of the human or animal body or for the manufacture of pharmaceutical preparations.

The compound of formula Ia is disclosed, for example, in European Patent Application No. 165 904 as "5-(p-cyanophenyl)-5,6,7,8-tetrahydroimidazo[1,5-a]pyridine hydrochloride" and, on account of its properties inhibiting the enzyme aromatase, is proposed inter alia for the treatment of oestrogen-dependent diseases, especially oestrogen-dependent breast cancer in postmenopausal women.

The above-mentioned patent application also describes the preparation of the compound of formula Ia. In most cases it is effected by dissolving the free base in a small amount of acetone and adding an ethereal HCl solution. One example also describes the direct preparation of the compound of formula Ia by cyclisation of 4-[4-chloro-4-(p-cyanophenyl)-n-butyl]-1H-imidazole dissolved in chloroform. In all cases, the compound of formula Ia is obtained in anhydrous form, as the anhydrate.

It has now been found that the crystals of the anhydrate of formula Ia can be in at least two different crystal modifications. One of those modifications, hereinafter referred to as "α-anhydrate", is characterised by the following lattice spacings (d values) and relative line intensities (intensity) of its X-ray powder pattern:

| d values [in Angstroem ($10^{-10}$ m)] | Intensity |
| --- | --- |
| 9.5 | very strong |
| 6.8 | very weak |
| 6.6 | very strong |
| 5.89 | medium |
| 5.10 | strong |
| 4.87 | medium |
| 4.75 | weak |
| 4.61 | strong |
| 4.30 | very weak |
| 4.19 | very strong |
| 4.01 | medium |
| 3.79 | medium |
| 3.61 | medium |
| 3.58 | medium |
| 3.47 | very strong |
| 3.37 | very weak |
| 3.30 | very strong |
| 3.23 | very weak |
| 3.03 | very weak |

The following remarks relating to the measuring method may be made (they apply analogously to all X-ray powder patterns given below): To determine the lattice spacings=interplanar spacings (d values), the diffraction pattern is recorded on film. The recording is made in transmission using a Guinier camera (Enraf-Nonius FR 552) and copper-$K_{\alpha 1}$ radiation (wavelength $\lambda = 1.54060$ Angstroem). For calibration purposes there is used a pattern of quartz recorded on the same film. The relative line intensities are estimated by visual inspection.

The second crystal modification of the anhydrate of formula Ia, hereinafter designated "β-anhydrate", is characterised by the following X-ray powder pattern:

| d values [in Angstroem ($10^{-10}$ m)] | Intensity |
| --- | --- |
| 12.1 | very strong |
| 7.3 | weak |
| 6.6 | very strong |
| 6.0 | very strong |
| 5.93 | very weak |
| 5.83 | strong |
| 4.61 | strong |
| 4.53 | medium |
| 4.46 | strong |
| 4.31 | medium |
| 4.13 | strong |
| 4.03 | medium |
| 3.99 | weak |
| 3.94 | medium |
| 3.66 | weak |
| 3.51 | very strong |
| 3.48 | strong |
| 3.40 | strong |
| 3.34 | strong |
| 3.28 | medium |
| 3.21 | strong |
| 3.11 | medium |
| 3.01 | weak |
| 2.97 | medium |

The crystals of the anhydrate of formula Ia-both the α- and the β-anhydrate-have the disadvantage that they are hygroscopic, that is to say they take up varying amounts of water as a function of the ambient humidity. Water is adsorbed even from relatively dry air, for example having a relative humidity of 33% or 44% (see Tables 1 and 2).

TABLE 1

Water absorption of the α-anhydrate of formula Ia at 44% relative humidity and T = 23° C. (in a climatic jar) as a function of time

| Time [days] | Water content [in %]*) |
| --- | --- |
| 0 | 0.62 |
| 4 | 2.43 |
| 7 | 2.82 |
| 11 | 3.12 |
| 15 | 3.19 |
| 18 | 3.28 |
| 21 | 3.32 |

*)basis dry weight of the anhydrate

TABLE 2

Water absorption of the α-anhydrate of formula Ia at 33% relative humidity and T = 23° C. (in a climatic jar) as a function of time

| Time [days] | Water content [in %]* |
|---|---|
| 0 | 0.62 |
| 4 | 0.75 |
| 7 | 0.85 |
| 11 | 1.00 |

*basis dry weight of the anhydrate

Because the crystals of the anhydrate of formula Ia are hygroscopic, their storage stability is considerably impaired. As a result, it is more difficult to process them into pharmaceutical preparations, especially into forms of administration suitable for oral administration, such as tablets.

Furthermore, there are at least two different crystal modifications of the anhydrate of formula Ia. This complicates the manufacture of pharmaceutical preparations, especially of solid preparations, because it is necessary always to reckon with conversion—partial or complete—of one modification into the other, or to take measures to prevent such conversion. Different crystal modifications can have different properties, for example as regards their micronisability, their general tablet-forming properties or their solubility. If there is inadvertently used instead of a given crystal modification X a different crystal modification Y which has formed from X, or a mixture of X and Y, then serious problems can arise in the manufacture of pharmaceutical preparations.

The problem underlying the present invention is therefore to provide a novel crystalline form of 4-(5,6,7,8-tetrahydroimidazo[1,5-a]pyridin-5-yl)-benzonitrile hydrochloride that does not have the disadvantages mentioned above and that, in particular, is stable even when stored for several years.

A novel crystalline form of 4-(5,6,7,8-tetrahydroimidazo[1,5-a]pyridin-5-yl)-benzonitrile hydrochloride has now been found which, surprisingly, does not have the disadvantages inherent in the anhydrate of formula Ia and is completely stable to storage under normal ambient conditions. This novel crystalline form is the crystalline form of 4-(5,6,7,8-tetrahydroimidazo[1,5-a]pyridin-5-yl)-benzonitrile hydrochloride hemihydrate having the formula I:

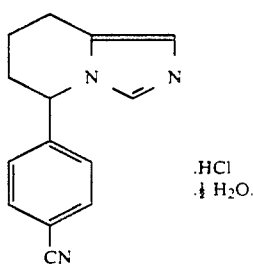

(I)

.HCl
.½ H₂O.

Surprisingly, it has been found that neither varying the relative humidity within a range of from approximately 10% to approximately 75% nor heating for 8 days at 35° or 50° C. brings about a detectable change in the X-ray powder pattern or the water content of the crystals of the hemihydrate of formula I (see Table 3).

TABLE 3

Water adsorption and water desorption experiments with the hemihydrate of formula I

| Conditions | Duration [days] | T [°C.] | Relative humidity [%] | Water content [%][1] |
|---|---|---|---|---|
| climatic jar | 2) | 23 | 75 (NaCl)[3] | 3.74 |
| climatic jar | 2) | 23 | 66 (Na₂CrO₄)[3] | 3.59 |
| climatic jar | 2) | 23 | 54 (Na₂Cr₂O₇)[3] | 3.54 |
| climatic jar | 2) | 23 | 33 (MgCl₂)[3] | 3.54 |
| climatic jar | 2) | 23 | 23 (CH₃COOK)[3] | 3.59 |
| climatic jar | 2) | 23 | 12 (LiCl)[3] | 3.54 |
| open vessel | 8 | 35 | ( 21%) | 3.54 |
| open vessel | 8 | 50 | ( 10%) | 3.44 |

[1]basis dry weight of the anhydrate; theoretical value for the hemihydrate of formula I: 3.47%
[2]after establishment of equilibrium
[3]climate adjustment using corresponding saturated aqueous solutions Table 3 shows that the crystals according to the invention of the hemihydrate of formula I have unlimited storage stability. This means that they can be stored as bulk goods ("batch") for several years without undergoing any change. In particular, they do not take up any more water, so that the content of active ingredient remains constant during storage and does not—as is the case with the known anhydrate of formula Ia—decrease continuously while the original weight remains the same. This is especially important in view of the extraordinary high effectiveness of the compound and the consequent low dosage used in humans, which is in the range of only one or a few milligrams (see below).

The crystals of the hemihydrate of formula I are characterised by the following lattice spacings (d values) and relative line intensities (intensity) of their X-ray powder pattern:

| d values [in Angstroem ( 10⁻¹⁰ m)] | Intensity |
|---|---|
| 13.4 | very strong |
| 9.5 | medium |
| 8.2 | weak |
| 7.5 | strong |
| 6.7 | very weak |
| 6.5 | very strong |
| 5.65 | very strong |
| 5.42 | strong |
| 5.34 | very strong |
| 5.15 | medium |
| 4.99 | medium |
| 4.84 | strong |
| 4.60 | strong |
| 4.51 | strong |
| 4.20 | strong |
| 4.09 | medium |
| 4.00 | strong |
| 3.83 | strong |
| 3.81 | medium |
| 3.76 | weak |
| 3.74 | medium |
| 3.66 | medium |
| 3.62 | strong |
| 3.56 | medium |
| 3.51 | medium |
| 3.40 | very weak |
| 3.35 | medium |
| 3.29 | very weak |
| 3.25 | strong |
| 3.21 | weak |
| 3.19 | weak |
| 3.15 | medium |
| 3.13 | very weak |
| 3.04 | strong |
| 3.01 | weak |

The crystals of the hemihydrate of formula I are further characterised by their elemental analysis, which is in accordance with the values calculated for the molecular formula $C_{14}H_{13}N_3 \cdot HCl \cdot \tfrac{1}{2}H_2O$ (MW: 268.75): C 62.57%; H 5.63%; N 15.64%; Cl 13.19%.

Preferably, the invention relates to the crystals of the hemihydrate of formula I in substantially pure form.

The crystals of the hemihydrate of formula I are prepared in a manner known per se, for example by (a) reacting 4-(5,6,7,8-tetrahydroimidazo[1,5-a]pyridin-5-yl)-benzonitrile with hydrogen chloride in the presence of water, or (b) treating with water a form of 4-(5,6,7,8-tetrahydroimidazo[1,5-a]pyridin-5-yl)-benzonitrile hydrochloride that contains less water than does the hemihydrate of formula I to be prepared, or (c) removing water from a form of 4-(5,6,7,8-tetrahydroimidazo[1,5-a]pyridin-5-yl)-benzonitrile hydrochloride that contains more water than does the hemihydrate of formula I to be prepared, or (d) converting a salt of 4-(5,6,7,8-tetrahydroimidazo[1,5-a]pyridin-5-yl)-benzonitrile other than the hydrochloride into the hydrochloride hemihydrate of formula I in the presence of water.

Process (a): Prior to the reaction, the free base 4-(5,6,7,8-tetrahydroimidazo[1,5-a]pyridin-5-yl)-benzonitrile used as starting material is preferably dissolved in an organic solvent, for example ethyl methyl ketone or, especially, acetone.

Preferably, the free base is converted into the hydrochloride hemihydrate of formula I using an aqueous hydrogen chloride solution. The concentration of the aqueous hydrogen chloride solution is not critical per se, but, in order to minimise losses in yield, the use of concentrated hydrochloric acid, especially 37% hydrochloric acid, is preferred.

The reaction temperature is, for example, from 0° to 70° C., advantageously from 20° to 55° C.; the reaction is carried out especially at room temperature.

Process (b): The treatment with water of, especially, solid forms of 4-(5,6,7,8-tetrahydroimidazo[1,5-a]pyridin-5-yl)-benzonitrile hydrochloride that contain less water than does the hemihydrate of formula I according to the invention, for example of the above-mentioned α- or β-anhydrate of formula Ia, is carried out in customary manner by the action of at least that amount of water required to form the hemihydrate. The water is preferably in the liquid or gaseous state.

In the case of treatment with water in the liquid state, the form of 4-(5,6,7,8-tetrahydroimidazo[1,5-a]pyridin-5-yl)-benzonitrile hydrochloride having a low water content is suspended or dissolved in water or in an aqueous solvent mixture and then the crystals of the hemihydrate of formula I are isolated in customary manner. In the case of a solution, the hemihydrate of formula I must first be caused to crystallise in customary manner, for example by concentrating the solution, i.e. evaporating off part of the solution, adding a water-miscible solvent in which the hemihydrate of formula I is less soluble than in water, or by reducing the temperature. In a preferred form, crystallisation of the hemihydrate of formula I is initiated or accelerated by inoculation with seed crystals of the hemihydrate of formula I.

In the case of treatment with water in the gaseous state, the starting material is exposed to an atmosphere containing water vapour, e.g. moist air. The exposure time required for the conversion decreases as the relative humidity increases. At room temperature, the relative humidity is preferably approximately from 50 to 70%.

The product is isolated in customary manner, for example by centrifugation, filtration or pressure filtration (filtration with suction). The product is advantageously dried at 20°–30° C.; vacuum drying at 20° C. is preferred.

Process (c): Suitable forms of 4-(5,6,7,8-tetrahydroimidazo[1,5-a]pyridin-5-yl)-benzonitrile hydrochloride are especially those which are solid or liquid, for example moist crystals, aqueous suspensions, aqueous solutions, suspensions in aqueous solvent mixtures, or solutions in aqueous solvent mixtures.

The excess water is removed, for example, by drying, advantageously at 20°–30° C. and preferably in vacuo at 20° C.

In the case of solutions of suspensions, the crystals of the hemihydrate of formula I are preferably isolated before drying, for example as indicated in process (b) by crystallisation and/or centrifugation, filtration or pressure filtration. However, the solutions or suspensions may also be concentrated directly by evaporation in vacuo, for example at 20°–30° C.

Process (d): A salt other than the hydrochloride is preferably a pharmaceutically acceptable salt.

Process (d) is known per se; for example, the salt other than the hydrochloride is dissolved in a water-containing solvent or solvent mixture, and an excess of chloride ions or, especially, hydrogen chloride is added. Preferably, the solvent selected is one in which the hydrochloride is less soluble than is the salt used as starting material.

The salt other than the hydrochloride that is required as starting material is prepared, for example, by reacting the free base 4-(5,6,7,8-tetrahydroimidazo[1,5-a]pyridin-5-yl)-benzonitrile with the corresponding acid.

The present invention relates also to pharmaceutical preparations that contain the crystals of the hemihydrate of formula I as active ingredient. Preparations for enteral, especially oral, administration are especially preferred. The preparations contain the active ingredient on its own or, preferably, together with one or more pharmaceutically acceptable carriers. The dosage of the active ingredient depends upon the disease to be treated, and upon the species, its age, weight and individual condition, and upon the mode of administration.

The pharmaceutical preparations contain from approximately 0.1% to approximately 40% active ingredient, forms of administration that are in single dose form preferably containing from approximately 0.1% to approximately 20% active ingredient, and forms of administration that are not in single dose form preferably containing from approximately 0.1% to approximately 10% active ingredient. Dosage unit forms, such as dragées, tablets or capsules, contain from approximately 0.1 mg to approximately 20 mg, preferably from approximately 1 mg to approximately 4 mg, of active ingredient.

The pharmaceutical preparations of the present invention are manufactured in a manner known per se, for example by means of conventional mixing, granulating, confectioning, dissolving or lyophilising processes. For example, pharmaceutical compositions for oral administration can be obtained by combining the active ingredient with one or more solid carriers, optionally granulating a resulting mixture and processing the mixture or granulate, if desired and/or appropriate, by the addition of additional adjuncts, to form tablets or dragée cores.

Suitable carriers are especially fillers, such as sugars, for example lactose, saccharose, mannitol or sorbitol, cellulose preparations and/or calcium phosphates, for example tri-calcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate.

Additional adjuncts are especially flow-regulating agents and lubricants, for example silicic acid, talc, stearic acid or salts thereof, such as magnesium or calcium stearate, and/or polyethylene glycol, or derivatives thereof.

Dragée cores can be provided with suitable coatings which may be resistant to gastric juices, there being used inter alia concentrated sugar solutions which may contain gum arabic, talc, polyvinylpyrrolidone, polyethylene glycol and/or titanium dioxide, or lacquer solutions in suitable organic solvents or solvent mixtures or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Pharmaceutical compositions for oral administration are also dry-fill capsules consisting of gelatine, and soft sealed capsules consisting of gelatine and a plasticiser, such as glycerine or sorbitol. The dry-fill capsules may contain the active ingredient in the form of a granulate, for example in admixture with fillers, such as corn starch, binders and/or glidants, such as talc or magnesium stearate, and optionally stabilisers. In soft capsules, the active ingredient is preferably dissolved or suspended in suitable liquid adjuncts, such as fatty oils, paraffin oil or liquid polyethylene glycols, it likewise being possible to add stabilisers.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols.

The invention relates also to a method of treating diseases in mammals, including humans, which respond to an inhibition of the activity of the enzyme aromatase or suppression of oestrogen synthesis, for example oestrogen-dependent diseases, especially oestrogen-dependent tumours, for example oestrogen-dependent breast cancer (mammary tumours), or gynaecomastia. The hemihydrate of the present invention can be administered prophylactically or therapeutically. In a warm-blooded animal having a body weight of approximately 70 kg, a daily dose of from approximately 0.1 mg to approximately 20 mg, preferably from approximately 1 mg to approximately 4 mg, of the hemihydrate of the present invention is administered.

The following Examples serve to illustrate the present invention, but are not intended to limit the scope thereof in any way. Temperatures are given in degrees Celsius.

EXAMPLE 1

4-(5,6,7,8-Tetrahydroimidazo[1,5-a]pyridin-5-yl)-benzonitrile hydrochloride hemihydrate 33 kg of 4-(5,6,7,8-tetrahydroimidazo[1,5-a]pyridin-5-yl)-benzonitrile are introduced at 20°-25° into 200 l of acetone, with stirring. As soon as everything has dissolved, 1.56 l of water and 1.8 kg of active carbon, made into a slurry with 6 l of acetone, are added. After stirring for 45 minutes at 20°-25°, the batch is filtered and the residue is washed with 138 l of acetone. Approximately 12.5 of hydrochloric acid (37%) are introduced into the combined filtrates, with stirring at 20°-25°, until pH 2.5-1.0 is reached. The resulting suspension is then stirred for 3 hours at 20°-25° and centrifuged, and the residue is washed in portions with a total of 80 l of acetone. Vacuum drying at 20° yields the title compound in the form of a white crystalline powder.

X-ray powder pattern: lattice spacings/intensities as given above;

IR (Nujol): 3430 (strong), 3375 (strong), 2225 (strong) cm$^{-1}$;

Elemental analysis: $C_{14}H_{13}N_3 \cdot HCl \cdot \frac{1}{2}H_2O$ (MW: 268.75) calculated: C 62.57%; H 5.63%; N 15.64%; Cl 13.19%. found: C 62.53%; H 5.57%; N 15.66%; Cl 13.21%.

Determination of water content (according to Karl-Fischer): calculated: 3.35%[1]) found: 3.43%.

[1]) The theoretical water content calculated here (based on the molecular weight of the hemihydrate of formula I) is not at variance with the theoretical water content of the hemihydrate of formula I given in Table 3, which is based on the dry weight (=molecular weight) of the anhydrate.

The free base used as starting material is prepared as described in EP-A-165 904, especially by ring closure of 5-(3-chloropropyl)-1-(p-cyanophenylmethyl)-1H-imidazole with potassium tert.-butoxide in tetrahydrofuran (see Example 1 of EP-A-165 904).

EXAMPLE 2

4-(5,6,7,8-Tetrahydroimidazo[1,5-a]pyridin-5-yl)-benzonitrile hydrochloride hemihydrate 5.3 kg of 4-(5,6,7,8-tetrahydroimidazo[1,5-a]pyridin-5-yl)-benzonitrile hydrochloride (α-anhydrate) are introduced into a stirred mixture of 1.5 l of water and 4.2 l of acetone. The mixture is heated and stirred at 50°-55° until a clear solution is obtained. The solution is then cooled to 30° and inoculated with 5 g of 4-(5,6,7,8-tetrahydroimidazo[1,5-a]pyridin-5-yl)-benzonitrile hydrochloride hemihydrate. When crystallisation has begun, the mixture is cooled to 0° within a period of 45 minutes. 35 l of acetone are metered in at 0°-5° within a period of 1 hour. The suspension is then stirred for 2 hours at 0°-5° and centrifuged, and the crystalline residue is washed with 8 l of acetone. Drying in vacuo at 20° yields the title compound.

X-ray powder pattern: lattice spacings/intensities as given above;

IR (Nujol): 3430 (strong), 3375 (strong), 2225 (strong) cm$^{-1}$;

Elemental analysis: $C_{14}H_{13}N_3 \cdot HCl \cdot \frac{1}{2}H_2O$ (MW: 268.75) calculated: C 62.57%; H 5.63%; N 15.64%; Cl 13.19%. found: C 62.63%; H 5.58%; N 15.67%; Cl 13.25%.

Determination of water content (according to Karl-Fischer): calculated: 3.35%. found: 3.46%.

The α-anhydrate used as starting material is prepared as described in EP-A-165 904, that is to say by dissolving the free base in a small amount of acetone and neutralising with ethereal hydrogen chloride (see Example 1 of EP-A-165 904).

EXAMPLE 3

10,000 100 mg tablets are manufactured, each containing 2 mg of active ingredient:

| Composition: | |
|---|---|
| 4-(5,6,7,8-tetrahydroimidazo[1,5-a]pyridin-5-yl)-benzonitrile hydrochloride hemihydrate | 20.70 g |
| colloidal silica | 2.00 g |
| microcrystalline cellulose | 100.00 g |
| lactose, spray-dried | 817.30 g |
| magnesium stearate | 10.00 g |
| sodium carboxymethylcellulose | 50.00 g |
| | 1,000.00 g |

All the constituents of the tablet core are mixed together. When a homogeneous mixture has been obtained, it is compressed to form tablet cores.

EXAMPLE 4

10,000 100 mg tablets are manufactured, each containing 1 mg of active ingredient:

| Composition: | |
|---|---|
| 4-(5,6,7,8-tetrahydroimidazo[1,5-a]pyridin-5-yl)-benzonitrile hydrochloride hemihydrate | 10.35 g |
| crystalline lactose | 739.65 g |
| microcrystalline cellulose | 230.00 g |
| colloidal silica | 10.00 g |
| magnesium stearate | 10.00 g |
| | 1,000.00 g |

All the constituents of the tablet core are mixed together. When a homogeneous mixture has been obtained, it is compressed to form tablet cores.

EXAMPLE 5

Preparation of 10,000 tablets each containing 1 mg of the active ingredient:

| Formula: | |
|---|---|
| 4-(5,6,7,8-tetrahydroimidazo[1,5-a]pyridin-5-yl)-benzonitrile hydrochloride hemihydrate | 10.35 g |
| Lactose, crystalline | 629.65 g |
| Maize starch | 350.00 g |
| Magnesium stearate | 10.00 g |
| | 1000.00 g |

The dry substance, the ground lactose and a part of maize starch are mixed. This mixture is granulated with starch paste, prepared from a further part of maize starch and water, dried and milled. After admixing the remaining maize starch and the magnesium stearate the homogeneous mixture is compressed into tablets containing the stated amount of active substance.

EXAMPLE 6

Preparation of 10,000 tablets each containing 2 mg of the active ingredient:

| Formula: | |
|---|---|
| 4-(5,6,7,8-tetrahydroimidazo[1,5-a]pyridin-5-yl)-benzonitrile hydrochloride hemihydrate | 20.70 g |
| Lactose, crystalline | 619.30 g |
| Maize starch | 350.00 g |
| Magnesium stearate | 10.00 g |
| | 1000.00 g |

The dry substance, the ground lactose and a part of maize starch are mixed. This mixture is granulated with starch paste, prepared from a further part of maize starch and water, dried and milled. After admixing the remaining maize starch and the magnesium stearate the homogeneous mixture is compressed into tablets containing the stated amount of active substance.

EXAMPLE 7

Preparation of 10,000 tablets each containing 1 mg of the active ingredient:

| Formula: | |
|---|---|
| 4-(5,6,7,8-tetrahydroimidazo[1,5-a]pyridin-5-yl)-benzonitrile hydrochloride hemihydrate | 10.35 g |
| Silicium dioxide, colloidal (Silica aerogel) | 2.00 g |
| Cellulose, microcrystalline | 373.00 g |
| Hydroxypropylmethylcellulose | 20.00 g |
| Lactose, ground | 539.65 g |
| Magnesium stearate | 5.00 g |
| Polyvinyl-polypyrrolidone XL (cross-linked) | 50.00 g |
| | 1000.00 g |

The drug substance is mixed with a part of lactose and sieved. This premix is blended with hydroxypropylmethylcellulose, part of microcrystalline cellulose and the remaining lactose. This mixture is granulated with water, dried and milled. After admixing the remaining ingredients the homogeneous mixture is compressed into tablets containing the stated amount of active substance.

EXAMPLE 8

Preparation of 10,000 tablets each containing 2 mg of the active ingredient:

| Formula: | |
|---|---|
| 4-(5,6,7,8-tetrahydroimidazo[1,5-a]pyridin-5-yl)-benzonitrile hydrochloride hemihydrate | 20.70 g |
| Silicium dioxide, colloidal (Silica aerogel) | 2.00 g |
| Cellulose, microcrystalline | 373.00 g |
| Hydroxypropylmethylcellulose | 20.00 g |
| Lactose, ground | 529.30 g |
| Magnesium stearate | 5.00 g |
| Polyvinyl-polypyrrolidone XL (cross-linked) | 50.00 g |
| | 1000.00 g |

The drug substance is mixed with a part of lactose and sieved. This premix is blended with hydroxypropylmethylcellulose, part of microcrystalline cellulose and the remaining lactose. This mixture is granulated with water, dried and milled. After admixing the remaining ingredients the homogeneous mixture is compressed into tablets containing the stated amount of active substance.

I claim:

1. Crystalline 4-(5,6,7,8-tetrahydroimidazo[1,5-a]pyridin-5-yl)-benzonitrile hydrochloride hemihydrate in substantially pure form.

2. Crystalline 4-(5,6,7,8-tetrahydroimidazo[1,5-a]pyridin-5-yl)-benzonitrile hydrochloride hemihydrate according to claim 1, the X-ray powder pattern of which (Guinier camera, copper-$K_{\alpha 1}$ radiation) exhibits the following lattice spacings (d values) and relative line intensities (intensity):

| d values [in Angstroem ($10^{-10}$ m)] | Intensity |
|---|---|
| 13.4 | very strong |
| 9.5 | medium |
| 8.2 | weak |
| 7.5 | strong |
| 6.7 | very weak |
| 6.5 | very strong |
| 5.65 | very strong |
| 5.42 | strong |
| 5.34 | very strong |
| 5.15 | medium |
| 4.99 | medium |
| 4.84 | strong |
| 4.60 | strong |
| 4.51 | strong |
| 4.20 | strong |
| 4.09 | medium |
| 4.00 | strong |
| 3.83 | strong |
| 3.81 | medium |
| 3.76 | weak |
| 3.74 | medium |
| 3.66 | medium |
| 3.62 | strong |
| 3.56 | medium |
| 3.51 | medium |
| 3.40 | very weak |
| 3.35 | medium |
| 3.29 | very weak |
| 3.25 | strong |
| 3.21 | weak |
| 3.19 | weak |
| 3.15 | medium |
| 3.13 | very weak |
| 3.04 | strong |
| 3.01 | weak |

3. A method of inhibiting aromatase activity and suppressing estrogen synthesis which comprises administering to a mammal in need thereof an estrogen synthesis suppressing effective amount of the compound according to claim 1.

4. A method of inhibiting aromatase activity and suppressing estrogen synthesis which comprises administering to a mammal in need thereof an estrogen synthesis suppressing effective amount of the compound according to claim 2.

5. A method of treatment of diseases responsive to aromatase inhibition which comprises administering to a mammal in need thereof an aromatase-inhibiting effective amount of the compound according to claim 1.

6. A method of treatment of diseases responsive to aromatase inhibition which comprises administering to a mammal in need thereof an aromatase-inhibiting effective amount of the compound according to claim 2.

* * * * *